United States Patent

Nieder et al.

[11] Patent Number: 5,888,207
[45] Date of Patent: Mar. 30, 1999

[54] SADDLE-TYPE HIP PROSTHESIS

[75] Inventors: Elmar Nieder, deceased, late of Jork; Arnold Keller, Kayhude, both of Germany

[73] Assignees: GMT Gesellschaft für medizinische Technik mbH; Waldemar Link GmbH & Co. KG, both of Hamburg, Germany

[21] Appl. No.: 859,736

[22] Filed: May 21, 1997

[30] Foreign Application Priority Data

May 25, 1996 [DE] Germany .................. 196 21 269.3

[51] Int. Cl.⁶ ...................................................... A61F 2/36
[52] U.S. Cl. ................................. 623/23; 623/22
[58] Field of Search ................. 623/18, 20, 22, 623/23

[56] References Cited

U.S. PATENT DOCUMENTS

| 4,645,507 | 2/1987 | Engelbrecht et al. | 623/23 |
| 5,030,238 | 7/1991 | Nieder et al. | 623/23 |

*Primary Examiner*—Randy C. Shay
*Attorney, Agent, or Firm*—Henry M. Feiereisen

[57] ABSTRACT

A saddle-type prosthesis for replacement of a hip joint; includes a shank assembly for engagement in a femur, a saddle-shaped head having a seat to form a bearing area for engagement by a portion of a pelvic bone, and a mounting for so coupling the saddle-shaped head to the shank assembly as to permit a pivoting of the saddle-shaped head relative to the shank assembly about at least two predetermined axes for rotation with at least two degrees of freedom wherein one of the predetermined axes is positioned above the bearing area of the saddle-shaped head.

40 Claims, 4 Drawing Sheets

SADDLE-TYPE HIP PROSTHESIS

BACKGROUND OF THE INVENTION

The present invention generally refers to prostheses, and more particularly to a hip prosthesis for total replacement of a hip joint, including a shank anchored in the bone canal of the femur and a saddle-shaped head connected to the shank and rotationally movable with respect to the shank with at least two degrees of freedom, with the saddle-like head being formed with a bearing seat for providing a support for a portion of a pelvic bone.

European Pat. No. EP-A-0 300 131 A1 describes a saddle-type prosthesis, with the saddle-shaped head being rotatable relative to the shank about a transverse axis which extends substantially in longitudinal direction of the leg and is positioned parallel offset with respect to the longitudinal shank axis. Thus, the saddle-shaped head is rotationally movable relative to the shank with one degree of freedom in order to enable an outer or inner rotation of the leg. Additional rotational movements and pivot movements of the leg, i.e. bending and stretching or abduction and adduction are effected by this saddle-type prosthesis through a motion between the pelvic bone and saddle-shaped head, whereby the seat of the saddle-shaped head is flat and open to enable movements in longitudinal direction thereof as well as transversely thereto. Thus, in conjunction with the pivot joint that allows outer and inner rotations within the prosthesis, the leg movement attained by this type of prosthesis resembles the mobility achieved by a ball joint, so that such saddle-type prostheses have been frequently used for replacement of hip joints. Practice has shown however that the saddle-shaped head, as a result of the relative open configuration of the seat, has a tendency during the initial months after surgery to migrate from its bony bearing or to become disengaged therefrom. Later on, this phenomena is not experienced as typically a tight tissue capsule will build up around the metallic saddle-shaped head and ossify in many cases. In addition, the relatively small seat or bearing surface of the pelvic bone upon the saddle-shaped head may also cause slight upward migration of the saddle-shaped head in the pelvic bone, or even a fracture of the pelvic bone above the saddle-shaped head when the bone is subject to excessive stress.

European Pat. No: EP-A-0 300 131 A1 further discloses a saddle-type prosthesis of a type having a ball joint additionally disposed beneath the saddle-shaped head at a location between the saddle-shaped head and the shank, and permitting to a limited degree rotational movements about further axes that are inclined relative to the transverse saddle axis so that the saddle-shaped head is rotationally mobile relative to the shank with three degrees of freedom. The superimposed disposition of two joints, i.e. the ball joint, on the one hand, and the joint between the open saddle-shaped head and the pelvic bone, on the other hand, lead however to instability of the saddle-shaped head that may cause a tilting. Therefore, this saddle-type prosthesis has not been used in practice.

SUMMARY OF THE INVENTION

It is thus an object of the present invention to provide an improved saddle-type prosthesis, obviating the afore-stated drawbacks.

In particular, it is an object of the present invention to provide an improved saddle-type prosthesis which eliminates any instability or tilting of the saddle-shaped head while yet counteracting a migration or disengagement of the pelvic bone from the saddle-shaped head and/or upward migration of the saddle-shaped head in the pelvic bone and/or fracture thereof above the saddle-shaped head.

These objects, and others which will become apparent hereinafter, are attained in accordance with the present invention by providing a shank assembly for engagement in a femur; a saddle-shaped head having a seat to form a bearing area for support of a portion of a pelvic bone; and a connection assembly for so coupling the saddle-shaped head to the shank assembly as to permit a turning of the saddle-shaped head relative to the shank assembly about at least two predetermined rotational or pivot axes to effect a rotation with at least two degrees of freedom wherein at least one of the predetermined axes is positioned above the bearing area of the saddle-shaped head to allow a turning of the saddle-shaped head relative to the shank during bending/stretching and/or abduction/adduction of the thigh.

The present invention is based on the recognition to rotatably support the saddle-shaped head above its bearing area as opposed to the prior art in which the saddle-shaped head is rotatably supported below the saddle-shaped head. Thus, the contact area of the pelvic bone, receiving the weight forces, is swingably suspended in the saddle-shaped head so that the load transfer of the weight forces from the pelvic bone to the saddle-shaped head occurs below the suspension thereby allowing the saddle-shaped head to constantly seek the most stable position in accordance with the direction of the impacting weight forces when the prosthesis supports a portion of the body weight so that the risk of tilting is eliminated, without adversely affecting rotational or pivot motions about the respective rotational or pivot axis. The suspension formed in the saddle-shaped head affords the conditions for attaining proper rotational and pivot motions of the femur and creates a reliable force transmission. An upward migration of the saddle-shaped head or a fracture of the pelvic bone is counteracted by dimensioning the saddle as wide as possible in order to allow a load transmission over a large area.

According to another feature of the present invention, the saddle-shaped head is provided with two horns, with the seat extending therebetween. Suitably, both horns should only slightly diverge to prevent the saddle from migrating or becoming disengaged from the cavity in the pelvic bone.

Both, the provision of a wide bearing area and slightly diverging horns of a saddle-shaped head would result in the conventional saddle-type prosthesis described in European Pat. No: EP-A-0 300 131 A1 in a restriction of the mobility between the bone and the saddle-shaped head. In order to compensate such a restriction without relinquishing the formation of a wide bearing area and slightly diverging horns, all three degrees of freedom of the movement that must be transmitted by the saddle-type prosthesis and are generally achieved only by use of a ball joint, should be shifted from the articulation between bone and saddle-shaped head into the prosthetic construction, without adversely affecting the overall stability thereof. In general, it is conceivable to shift only one of the rotational or pivot axes, responsible for bending and stretching or abduction and adduction of the thigh, preferably the one pivot axis extending between the opposing horns, into the prosthesis and to retain the other pivot axis on the surface of the saddle seat, with the other pivot axis preferably extending between the horns transversely across the seat. As a result, the bearing area could be significantly enlarged for a support of the pelvic bone upon the saddle-shaped head so as to reduce the likelihood of an upward migration and/or fracture of the pelvic bone above the saddle-shaped head. It is also conceivable to reduce the divergence of the horns to effect a better guidance of an edge face of the pelvic bone in the saddle and to thereby decrease the likelihood of a post-operative migration or disengagement of the pelvic bone from the saddle seat. Such a pivoted support of the pelvic bone in the saddle-shaped head and a pivoted suspension of the saddle-shaped head on the shank still results in a good leg mobility during bending/stretching as well as abduction/adduction or combination of these two motions despite the restriction of the mobility by the saddle with wider load-receiving area and less diverging horns in the joint between the saddle and the bone at a substantially perpendicular alignment of both axes. It is however also possible to shift only the one pivot axis that extends transversely across the saddle seat from one horn to the other horn, into the prosthesis and to retain the pivot axis extending between opposing horns upon the surface of the saddle seat.

According to a preferred embodiment of the present invention, both rotational or pivot axes required for enabling a combined bending/stretching and abduction/adduction are shifted into the prosthesis in order to effect a further enlargement of the load-receiving bearing area and/or narrowing of the seat between the horns to thereby achieve the afore-described results. Preferably, a cardanic suspension of the saddle-shaped head by swingably mounting the saddle-shaped head preferably in a ring segment which in turn is rotatably supported independent from the saddle-shaped head in a forked mounting. This cardanic suspension permits, on the one hand, a rotation of the shank assembly and thus of the thigh for combined bending/stretching motions and abduction/adduction motions with two degrees of freedom and at relatively great pivot angles relative to the saddle-shaped head, and, on the other hand, an engagement of the saddle-shaped head during surgery in such disposition with the pelvic bone as to best suit the anatomy of the patient, for example to a partially destroyed pelvic bone.

According to another feature of the present invention, the forked mounting is additionally rotatable relative to the shank assembly about a rotational axis which coincides substantially with the longitudinal axis of the leg in order to permit also an outer/inner rotation of the thigh relative to the pelvis and to afford the patient a leg mobility that resembles substantially the leg mobility of a natural hip joint.

In principal, the pelvic bone can be slightly pivoted within the prosthesis in the saddle-shaped head despite the three rotational degrees of freedom in order to optionally increase the pivot angle which is limited and predetermined by the construction of the prosthesis. The capability of the pelvic bone to pivot in the saddle-shaped head can e.g. be effected by providing a greater space between the pelvic bone and the opposing inner surfaces of the horns, and/or by polishing their surfaces to prevent a bony growth. On the other hand, it is now also possible to substantially or completely immobilize the pelvic bone through a respective guidance or fixation in the saddle-shaped head in order to securely prevent a post-surgical migration or disengagement of the pelvic bone from the saddle-shaped head.

The guidance may suitably include opposing guide surfaces that bear against opposite bone surfaces of the pelvic bone and are interconnected by the bearing area which carries the pelvic bone in the saddle-shaped head. Preferably, the guidance is of trough-shaped configuration and is defined by a substantially U-shaped cross section, with the facing inner sides of the horns forming the guide surfaces.

It is also conceivable to so configure the saddle in an anatomically correct manner, possibly after making a replica of a natural pelvic model that the inner surfaces of the saddle bear upon the bone throughout, and further to so coat the surface of the saddle as to promote a growth of bone. In the latter case, the fixation is preferably attained by forming the inner sides of the horns that bear against the bone and/or the support area with irregular surfaces to allow a growth of bony material and thereby create a permanent connection between the bone and the saddle-shaped head. Alternatively, it is also conceivable to anchor the edge face of the pelvic bone carried by the bearing area and engaging the guidance, by means of bone cement or by screws upon the saddle-shaped head, with the screws suitably received in transverse bores extending through one of the horns and terminating on the opposing side of the seat in form of an aligned blind bore with inner thread.

In order to provide a great pivot angle during interaction between the prosthesis and the pelvic bone, it is advantageous to pass one of both rotational or pivot axes of the cardanic suspension in parallel disposition to a longitudinal axis of the saddle seat between the opposing horns of the saddle-shaped head, preferably in a symmetrical plane that divides the saddle-shaped head in two halves, with each half accommodating a horn, while the other rotational or pivot axis traverses, preferably perpendicular thereto, both horns transversely to the longitudinal axis of the saddle seat, and is suitably oriented also in the plane of symmetry of the saddle-shaped head. The rotating or pivot axes preferably extend through the center of gravity of the saddle-shaped head or intersect above the center of gravity in order to prevent rotation or pivoting about one or both axes as a result of the own weight of the saddle-shaped head.

It is not necessarily required that both rotational or pivot axes and the rotational axis intersect each other at a right angle in order to generate the desired three degrees of freedom of the movement. A preferred embodiment provides however a Cartesian alignment of the three axes because in this case, the motion during pivoting and/or turning of the leg best resembles the natural movement in the anatomic hip joint.

According to yet another feature of the present invention, the overall size of the prosthesis in the area of the saddle-shaped head and its suspension is kept small by so ensuring a pivoting of the saddle-shaped head about one of both rotational or pivot axes that a ring segment is displaceably supported in a complementary ring-shaped outer guide groove along the underside of the saddle-shaped head while the other one of the two rotational or pivot axes are defined by a pivot bearing in which the ring segment is rotatably supported relative to the fork of the mounting. Suitably, the two rotational or pivot axes defined by the guide groove on the one hand, and by the pivot bearing on the other hand, extend perpendicular to one another. Preferably, the guide groove is recessed in a spherically rounded outer surface of the saddle-shaped head concentrically with respect to the rotational or pivot axis which extends in longitudinal direction of the saddle seat, whereby the guide groove extends suitably over an angle of 260°–310°, preferably from 270°–300° while the ring segment extends preferably over a circumferential angle of about 180° so that the ring segment is able to pivot from a center position to each side by about 45°–60° relative to the saddle-shaped head.

Preferably, the saddle-type prosthesis according to the present invention includes several detachably connected components, i.e. the saddle-shaped head, the ring segment shiftable in the guide groove of the saddle-shaped head, the forked mounting for suspension of the ring segment is suspended, an adapter or intermediate piece rotatable about the rotational axis and connected to a socket of the mounting for effecting a length compensation with respect to variations in the anatomy of patients and with respect to positional variations of the attachment of the saddle-shaped head, as well as the shank assembly on which the adapter is secured, preferably in a rigid manner.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
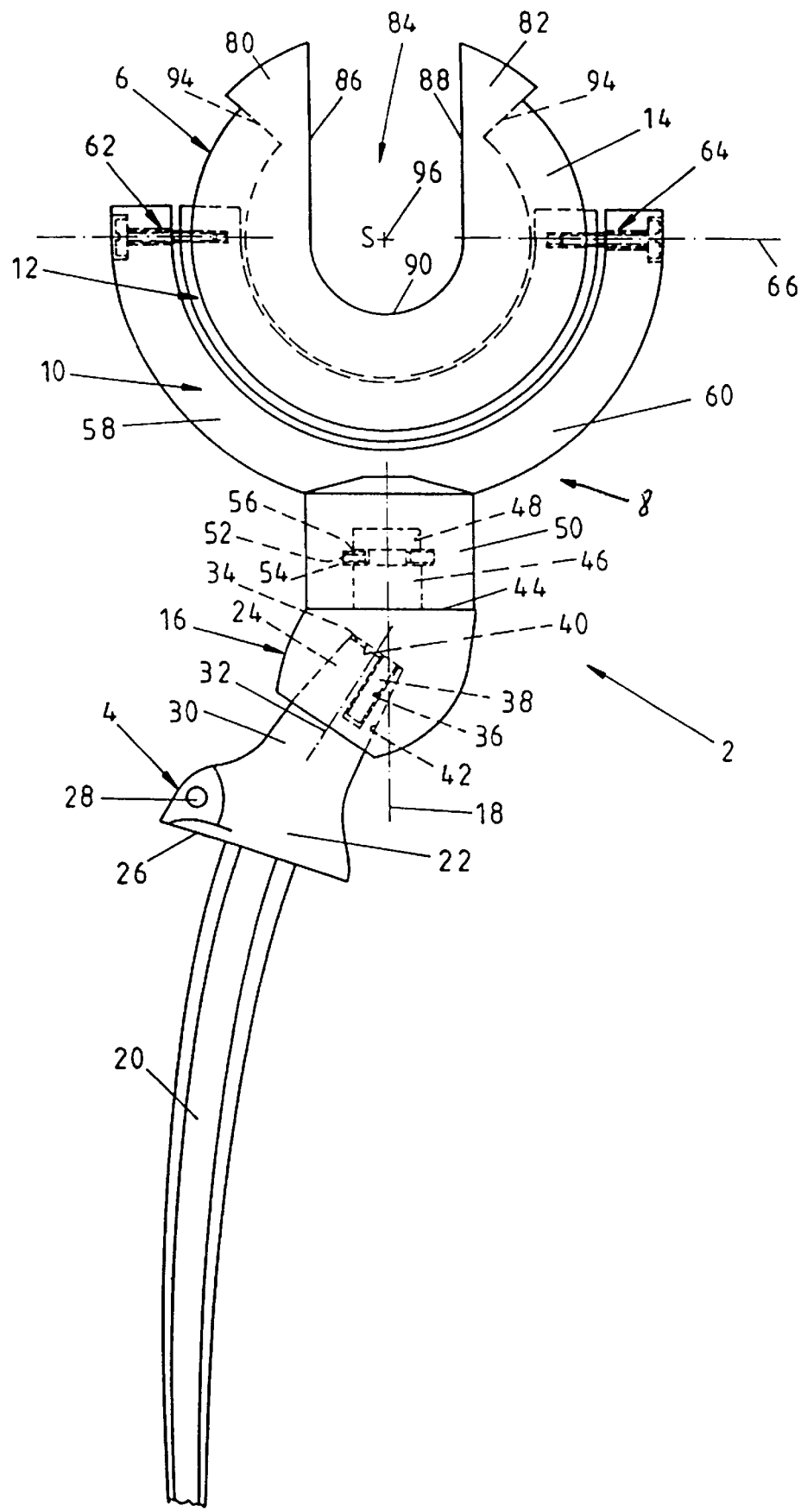
FIG. 1 is a front elevational side view of one embodiment of a saddle-type prosthesis according to the present invention.

Throughout all the Figures, the same or corresponding elements are generally indicated by the same reference numerals.

Turning now to the drawing, and in particular to FIG. 1, there is shown a front side elevational view of one embodiment of a saddle-type prosthesis according to the present invention, generally designated by reference numeral 2. The prosthesis 2 essentially includes a shank assembly, generally designated by reference numeral 4 and a saddle-shaped head, generally designated by reference numeral 6 and mounted to the shank assembly 4 via a cardanic suspension. The cardanic suspension of the saddle-shaped head 6 generally includes a mounting, generally designated by reference numeral 8 and including a fork 10 for rotatably supporting a ring segment 12 which is slidingly guided in a guide groove 14 on the underside of the saddle-shaped head 6. The prosthesis 2 further includes an intermediary piece or adapter, generally designated by reference numeral 16 which is placed over the shank assembly 4 for rotatably supporting the mounting 8 about an rotational axis 18 that coincides substantially with a longitudinal axis of the leg and forms a first predetermined rotational or pivot axis of the cardanic suspension.

The shank assembly 4 essentially includes an elongated shank 20 having an upper end formed with a collar 22 and a truncated cone shaped fastening pin 24 extending upwardly from the collar 22 for engagement by the adapter 16. Suitably, shank 20, collar 22 and fastening pin 24 are of single piece configuration.

The shank 20 is insertable in a medullary bone canal of a femur (not shown) and anchored therein by bone cement, or in a cementless manner through press-fit and formation of suitable surfaces promoting a growth of bone material. The collar 22 has a flat abutment end 26 which faces the shank 20 and, upon installation of the prosthesis 2, rests upon a respectively resected upper end of the femur. The shank 20 is slightly arched and tapers in direction of its collar-distal free end to best suit the curvature of the medullary canal in lateral direction.

The collar 22 is formed with a lateral eyelet 28 for facilitating an extraction of the shank 20 when the shank 20 is inserted in a preliminary stage for testing purposes into the medullary canal of the femur during preparation thereof. As shown in FIG. 1, the collar 22 tapers upwardly away from the shaft 20 and terminates in an essentially cylindrical center portion 30 of a diameter corresponding to the diameter of the lower wider end of the truncated cone shaped fastening pin 24. The fastening pin 24 tapers also upwards away from the collar 22 and defines a center axis 32 which is inclined in a lateral plane at an angle of about 35° relative to the rotational axis 18. The free end of the fastening pin 24 is defined by a flat end face 34 which has formed therein an eccentric blind bore 36 extending parallel to the center axis 32 of the fastening pin 24.

The adapter 16 is formed with a truncated cone shaped recess 42 to complement the configuration of the fastening pin 24. Connected integrally with the bottom 40 of the recess 42 is one end of a cylindrical bolt 38 which is engageable in the blind bore 36. The blind bore 36 and the cylindrical bolt 38, which is fitted in the blind bore 36 free of play, form together an anti-rotation device by which a rotation of the adapter 16 relative to the shank assembly 4 is prevented.

The adapter 16 includes convexly rounded outer surfaces and exhibits a flat upper end face 44 which extends perpendicular to the rotational axis 18 for support of a complementary lower end face of the mounting 8. The mounting 8 includes a socket 50 which is formed with a pocket 48 for engagement by a cylindrical pivot pin 46 that extends from the upper end face 44 of the adapter 16 and is rotatable about the rotational axis 18. The pivot pin 46 is so engaged in the complementary pocket 48 of the socket 50 as to be immobilized in axial direction. The pivot pin 46 and the pocket 48 are formed with aligned circumferential grooves 52, 54 along their neighboring perimeters for receiving a retainer ring or circlip 56 which prevents a removal of the pivot pin 46 from the pocket 48 while permitting an unhindered relative rotation of the mounting 8 and the adapter 16 about the rotational axis 18.

Figure 3:
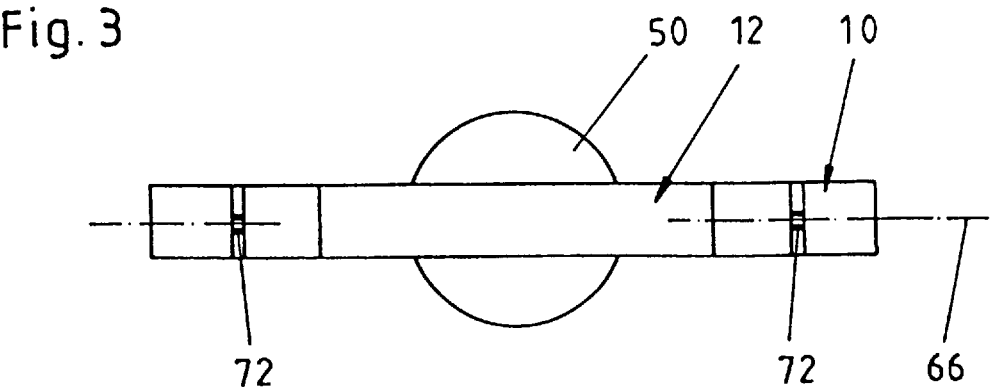
FIG. 3 is a top plan view of the mounting of FIG. 2.

The mounting 8 is further provided with a generally fork-shaped member 10 in form of two interconnected fork parts 58, 60 which form together with the socket 50 a single piece unit. The fork parts 58, 60 are shaped in the form of a quarter circle, with a square cross section, as shown in particular in FIG. 3. It is however certainly within the scope of the present invention to configure the fork parts 58, 60 with rounded edges or boundary surfaces.

The free end of both fork parts 58, 60 is provided with a pivot bearing 62, 64 for support of the ring segment 12 which, in vertical disposition of the rotational axis 18, is concentric to the fork 10. The pivot bearings 62, 64 are so disposed as to define pivot axes 66 that are aligned with one another to form a second predetermined rotational or pivot axis of the cardanic suspension.

Figure 2:
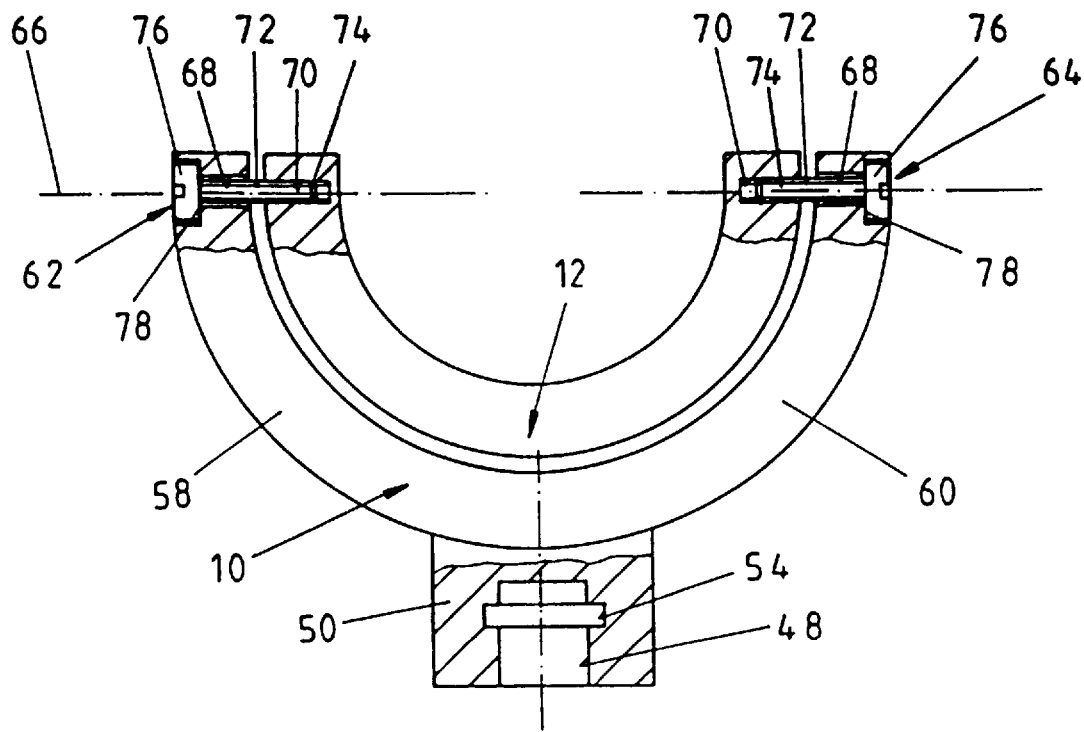
FIG. 2 is a fragmentary, partially sectional front view of the saddle-type prosthesis of FIG. 1, illustrating in detail the mounting thereof.

As shown in FIG. 2, each pivot bearing 62, 64 includes a transverse bore 68 formed in the free ends of the fork parts 58, 60 and in alignment with an opposing threaded bore 70 in the ring segment 12. A pivot pin 72 is threadably engaged with its forward screw thread 74 into the aligned bores 68, 70, and with its rear cylindrical shaft swingably supported in the transverse bore 68 of one of the fork parts 58, 60. In order to prevent the pivot pins 27 from escaping their seat, it may be suitable to add a small amount of biocompatible adhesive in the threaded bore 70 before screwing in the screw thread 74 of the pivot pin 72. Each pivot pin 72 has a head 76 of wider diameter for facilitating the engagement. The head 76 is received in a counterbore of the transverse bore 68 and impacts against a ring shoulder 78 to thereby keep the ring segment 12 and the fork 10 at a mutual constant distance.

Both, the ring segment 12 and the fork 10 extend over a circumferential angle of 180°, with the free ends of the ring segment 12 being slightly extended parallel to one another for accommodation of the pivot bearings 62, 64. The rotational or pivot axis 66 extends diametrical along a base of a semicircle which is circumscribed by the fork 10 and the ring segment 12.

As further shown in FIG. 1, the single piece saddle-shaped head 6 includes two opposing horns 80, 82 and a trough-shaped seat 84 extending between the horns 80, 82 for providing a bearing area for an edge face of the pelvic bone (not shown). The seat 84 has a generally U-shaped cross section, with facing parallel inner sides 86, 88 of the horns 80, 82 forming guide surfaces that bear against opposing bone areas of the edge face of the pelvic bone received in the seat 84. The guide surfaces 86, 88 are connected to one another by a semicylindrical bottom 90 of the seat 84, forming a bearing area 90 upon which the pelvic bone in the saddle-shaped head 6 rests. Depending on whether the pelvic bone is movably guided in the saddle-shaped head 6 or immovably secured therein, the guide surfaces 86, 88 and/or the bearing area 90 are polished to prevent a growth of bone, or exhibit uneven surfaces that promote a growth of bone.

Figure 4:
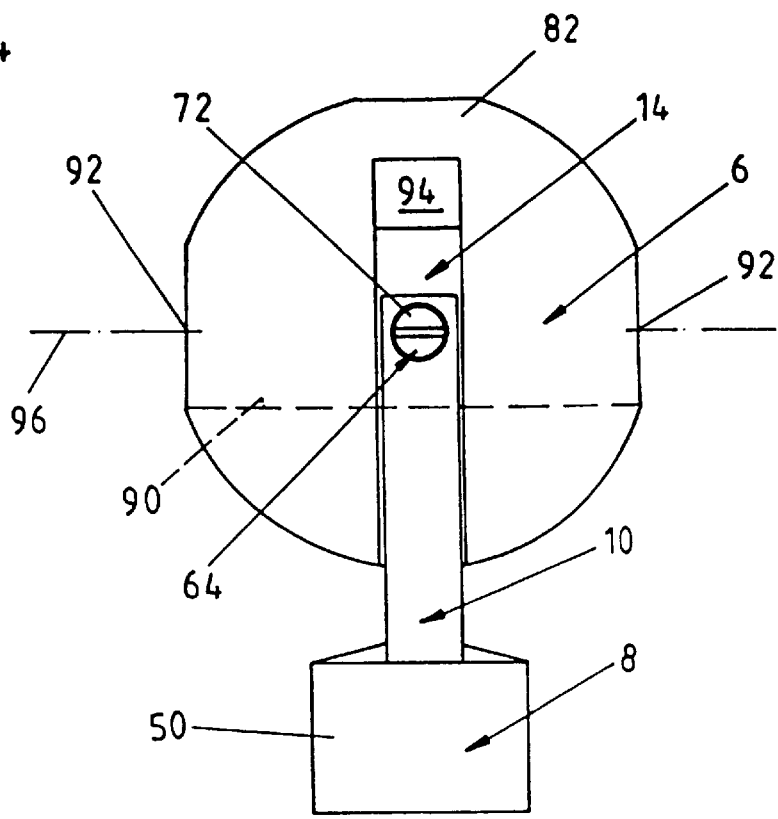
FIG. 4 is a side view of the saddle-type prosthesis of FIG. 1, illustrating in detail a saddle-shaped head suspended in the mounting.
Figure 5:
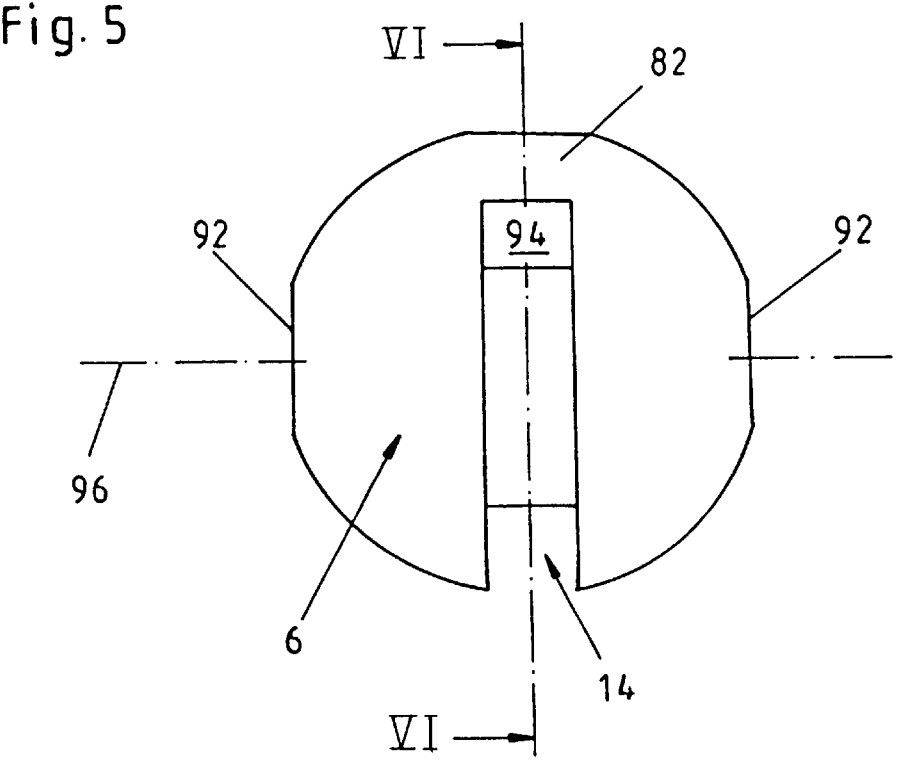
FIG. 5 is a side view of the saddle-shaped head of FIG. 4.
Figure 6:
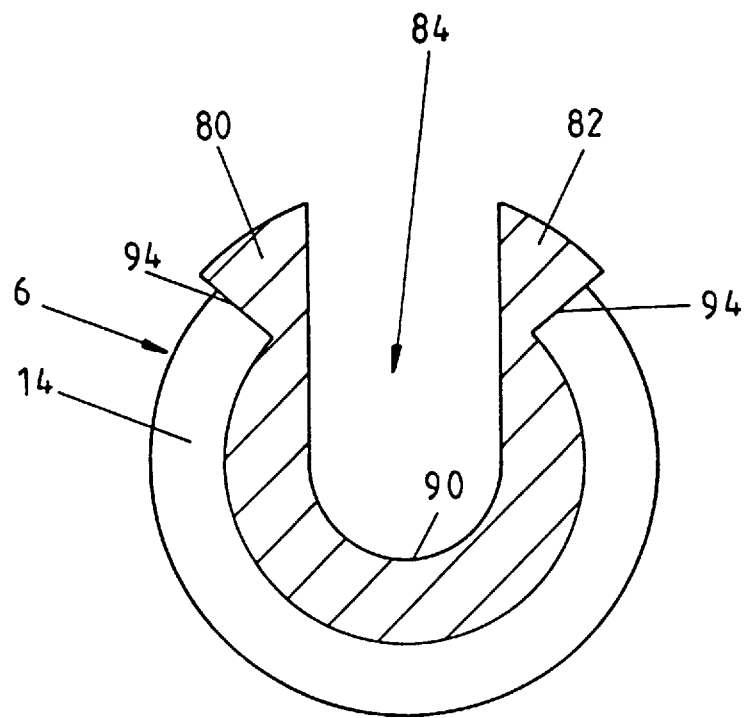
FIG. 6 is a sectional view of the saddle-shaped head taken along the line VI—VI in FIG. 5.

The saddle-shaped head 6 exhibits a generally spherical outer configuration with slightly flattened end faces 92 at their opposite end faces of the seat 84, as shown in FIGS. 4 and 5. The arcuate guide groove 14 for the ring segment 12 is formed through suitably recessing the underside and the opposing outer sides of the horns 80, 82, and extends transversely to the longitudinal direction of the trough-shaped seat 84 over a circumferential angle of about 270°. At the end faces, the guide groove 14 is flanked by flat stop surfaces 94 which extends essentially radial in relation to a third rotational or pivot axis 96 extending between the horns 80, 82 and forming a third predetermined axis of the cardanic suspension. The guide groove 14 and the ring segment 12 have complementary cross sections and smooth surfaces so that the ring segment 12 slides at low friction within the guide groove 14. The ring segment 12 or the saddle-shaped head 6 may be coated with a layer (not shown) of e.g. polyethylene in order to reduce the friction between the surfaces sliding upon one another. At a slightly wider thickness of the coating, e.g. in the form of an inlay within the saddle-shaped head 6, the coating may serve at the same time to captivate the saddle-shaped head 6 in the ring segment 12. This may be suitably effected by extending the inner circumference of the ring segment over an angle of slightly more than 180° so that the inlay has to be elastically deformed for mutually compression of the saddle-shaped head 6 and the ring segment 12 and thus may serve later as luxation safety mechanism that prevents a separation of the ring segment 12 from the saddle-shaped head 6 when being subject to a tension load.

Two of the three predetermined axes 18, 66, 96 of the cardanic suspension of the saddle-shaped head 6, namely the predetermined axis 96 about which the saddle-shaped head 6 and the ring segment 12 can pivot and which extends between the horns 80, 82 of the saddle-shaped head 6 in longitudinal direction of the seat 84, and the predetermined axis 66 extending transversely to the longitudinal direction of the seat 84 through the horns 80, 82, are disposed above the semicylindrical bearing area 90 to permit the saddle-shaped head 6 to constantly seek its most stable position with respect to the shank assembly 4 regardless of the direction of the weight force transmitted from the pelvic bone via the saddle-type prosthesis 2 onto the leg. Thus, a risk of tilting is eliminated.

Both predetermined rotational or pivot axes 66, 96 extend in two symmetrical planes of the saddle-shaped head 6 which subdivide the saddle-shaped head 6 in longitudinal direction in the center of the seat 84 and transversely thereto in two halves that are mirror images of one another. The three predetermined axes 18, 66, 96 of the cardanic suspension intersect one another also in the center of gravity S of the saddle-shaped head 6 so that no intrinsic angular momentum can act upon the saddle-shaped head 6 regardless of the alignment thereof.

The components of the saddle-type prosthesis, i.e. saddle-shaped head 6, the ring segment 12, the mounting 8, the adapter 16 and the shank assembly 4 are made of body-compatible implant material, for example a chromium-cobalt-molybdenum (CoCrMo) alloy, and are detachably connected together so as to be storable as kit containing components of different length dimensions to thereby enable an assembly to best suit the anatomy of the patient.

A replacement of a hip joint by a saddle-type prosthesis 2 according to the present invention is as follows:

Destroyed or diseased bone areas are removed and the upper end of the femur is resected for creating a flat bearing surface for support of the abutment end 26 of the collar 22 of the shank assembly 4. Subsequently, the medullary channel of the femur is prepared for insertion of the shank 20, and the pelvic bone is prepared in such a manner that either an edge face remaining after preceding resection of the destroyed or deceased bone areas, or a part of an edge of a cavity formed in the pelvic bone, is so adapted for receiving one of the horns 80, 82, as to match the bearing area formed by the saddle seat 84. A suitable adapter 16 is selected from the kit having such a length as to fit during preliminary insertion of the prosthesis 2 in an optimum manner between the shank assembly 4 and the mounting 8 that unites the saddle-shaped head 6 and the ring segment 2. The selected adapter 16 is then firmly secured in the mounting 8 by the circlip 56 so as to prevent a displacement in axial direction while still allowing a rotation thereof. After pushing down the shank 20 into the femur until the abutment end 26 lies against the bearing surface of the femur, and placement of the saddle-shaped head 6 over the prepared edge face of the pelvic bone, the leg is stretched and the truncated cone shaped fastening pin 24 is so inserted into the recess 42 of the adapter 16 that the cylindrical bolt 38 slides into the blind bore 36.

While the invention has been illustrated and described as embodied in a saddle-type prosthesis, it is not intended to be limited to the details shown since various modifications and structural changes may be made without departing in any way from the spirit of the present invention.

What is claimed as new and desired to be protected by Letters Patent is set forth in the appended claims:

1. A saddle-type prosthesis for replacement of a hip joint; comprising:
   a shank assembly for engagement in a femur located at a distal end of the prosthesis;
   a saddle-shaped head located at a proximal end of the prosthesis having a seat to form a bearing area for engagement by a portion of a pelvic bone; and
   a connecting means for so coupling the saddle-shaped head to the shank assembly as to permit a pivoting of the saddle-shaped head relative to the shank assembly about at least two predetermined axes for rotation with at least two degrees of freedom wherein one of the predetermined axes is positioned closer than the bearing area of the saddle-shaped head to the proximal end of the prosthesis.

2. The prosthesis of claim 1 wherein the saddle-shaped head is formed with two horns with the seat extending therebetween, said one predetermined axis extending in longitudinal direction of the seat between the opposing horns.

3. The prosthesis of claim 1 wherein the saddle-shaped head has two horns in opposite disposition, with the seat extending therebetween, said other one of the predetermined axes extending in longitudinal direction of the seat between the horns.

4. The prosthesis of claim 1 wherein the predetermined axes extend at least in a symmetrical plane of the saddle-shaped head.

5. The prosthesis of claim 1 wherein the predetermined axes extend through a center of gravity of the saddle-shaped head.

6. The prosthesis of claim 1 wherein the predetermined axes have a different orientation and extend at a location above the bearing area.

7. The prosthesis of claim 6 wherein rotations about the two predetermined axes are effected independent from one another.

8. The prosthesis of claim 6 wherein the two predetermined axes intersect each other.

9. The prosthesis of claim 6 wherein the two predetermined axes intersect in a plane at a right angle.

10. The prosthesis of claim 1 wherein the saddle-shaped head pivots cardanically relative to the shank assembly about the two predetermined axes and a third predetermined axis.

11. The prosthesis of claim 10 wherein the third predetermined axis is defined by a rotational axis essentially extending in longitudinal direction to permit an outer and inner rotation of a leg.

12. The prosthesis of claim 10 wherein the three predetermined axes intersect each other at a right angle.

13. The prosthesis of claim 10 wherein connecting means includes a mounting, said saddle-shaped head being suspended in the mounting for rotational movement about the two predetermined axes are.

14. The prosthesis of claim 13 wherein the mounting is rotatable about the third predetermined axis relative to the shank assembly.

15. The prosthesis of claim 13 wherein the mounting includes a socket rotatable about the third predetermined axis, and a fork projecting from the socket.

16. The prosthesis of claim 1 wherein the saddle-shaped head has formed therein an annular guide groove, and further comprising a ring segment swingably supported in the mounting and displaceable in the guide groove of the saddle-shaped head.

17. The prosthesis of claim 16 wherein the saddle-type head is formed with two horns with the seat extending therebetween, said the ring segment being so guided in the guide groove as to shift therein when pivoting about the other predetermined axis which extends between the horns.

18. The prosthesis of claim 16 wherein the guide groove extends about an angle of 260° to 310° across the underside of the saddle-shaped head.

19. The prosthesis of claim 18 wherein the guide groove extends about an angle of 270° to 300° across the underside of the saddle-shaped head.

20. The prosthesis of claim 16 wherein the guide groove is formed through recessing a spherically rounded outer surface of the saddle-shaped head.

21. The prosthesis of claim 16 wherein the ring segment is displaceably secured in the guide groove.

22. The prosthesis of claim 16 wherein the ring segment extends about a circumferential angle of 150° to 190°.

23. The prosthesis of claim 21 wherein the ring segment extends about a circumferential angle of 150° to 180°, said saddle-shaped head with the guide groove being loosely placed upon the ring segment.

24. The prosthesis of claim 16 wherein the ring segment extends about a circumferential angle of slightly more than 180° and is lockable in the guide groove of the saddle-shaped head.

25. The prosthesis of claim 1 wherein the seat of the saddle forms a bearing for the pelvic bone.

26. The prosthesis of claim 25 wherein the saddle-shaped head is formed with horns in opposite disposition, with the seat extending therebetween, said horns forming opposing inner surfaces to provide guide surfaces for adjoining bone areas of the pelvic bone.

27. The prosthesis of claim 1 wherein the bearing area is formed by a concavely shaped bottom of the seat.

28. The prosthesis of claim 1 wherein the seat has a trough-shaped configuration and exhibits a substantially U-shaped cross section.

29. The prosthesis of claim 1 wherein the bearing area is arched outwardly in a partially cylindrical manner.

30. The prosthesis of claim 26 wherein at least one element of the group consisting of guide surfaces and bearing area is polished.

31. The prosthesis of claim 26 wherein at least one element of the group consisting of guide surfaces and bearing area is formed as a surface promoting a growth of bony material.

32. The prosthesis of claim 16 wherein the saddle-shaped head, the ring segment, the connecting means, and the shank assembly are at least partially detachably connected together.

33. The prosthesis of claim 32, and further comprising a luxation safety mechanism positioned between at least one of the groupings consisting of ring segment and saddle, on the one hand, and mounting and shank assembly, on the other hand.

34. The prosthesis of claim 1, and further comprising an adapter positioned between the shank assembly and the mounting.

35. The prosthesis of claim 34 wherein the mounting is so connected to the adapter as to allow a rotation thereof while being prevented from a displacement in an axial direction.

36. The prosthesis of claim 34 wherein the adapter is formed with an upwardly projecting pivot pin for engagement in a pocket of the mounting.

37. The prosthesis of claim 36, and further comprising a retainer ring inserted in opposing circumferential grooves formed in the pocket and the pivot pin.

38. The prosthesis of claim 34 wherein the adapter is formed with a truncated cone shaped recess for receiving a truncated cone shaped pivot pin of the shank assembly.

39. The prosthesis of claim 38, and further comprising an anti-rotation device for preventing a rotation of the pivot pin in the recess.

40. The prosthesis of claim 39 wherein the anti-rotation mechanism is formed by a blind bore extending at a distance to a center axis of the pivot pin in parallel disposition and includes a cylindrical bolt arranged at a same distance from a center axis of the recess in parallel disposition thereto for engagement free from play into the blind bore.

* * * * *